US006249704B1

(12) United States Patent
Maltan et al.

(10) Patent No.: US 6,249,704 B1
(45) Date of Patent: Jun. 19, 2001

(54) LOW VOLTAGE STIMULATION TO ELICIT STOCHASTIC RESPONSE PATTERNS THAT ENHANCE THE EFFECTIVENESS OF A COCHLEAR IMPLANT

(75) Inventors: Albert A. Maltan, Stevenson Ranch; William Vanbrooks Harrison, Valencia, both of CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/371,725

(22) Filed: Aug. 10, 1999

Related U.S. Application Data

(60) Provisional application No. 60/096,191, filed on Aug. 11, 1998.

(51) Int. Cl.$^{7}$ .......... A61N 1/36

(52) U.S. Cl. .......... 607/57

(58) Field of Search .......... 607/55–57, 137; 623/10; 600/25

(56) References Cited

U.S. PATENT DOCUMENTS

| | | | |
|---|---|---|---|
| 4,357,497 | 11/1982 | Hochmair et al. | 179/107 E |
| 4,510,936 * | 4/1985 | Fourcin et al. | 607/56 |
| 5,095,904 * | 3/1992 | Seligman et al. | 607/56 |
| 5,271,397 | 12/1993 | Seligman et al. | 607/137 |
| 5,603,726 | 2/1997 | Schulman et al. | 607/57 |
| 5,674,264 | 10/1997 | Carter et al. | 607/57 |
| 5,758,651 | 6/1998 | Nygard et al. | 128/741 |
| 5,885,225 | 3/1999 | Keefe et al. | 600/559 |
| 6,078,838 * | 6/2000 | Rubinstein | 607/55 |

* cited by examiner

*Primary Examiner*—Jeffrey R. Jastrzab
(74) *Attorney, Agent, or Firm*—Bryant R. Gold

(57) ABSTRACT

A cochlear stimulation system includes a speech processing strategy that applies non-auditory-informative stimuli as well as auditory-informative stimuli to the same or neighboring sets of electrodes. The non-auditory-informative stimuli are applied to the auditory neural system for the purpose of influencing the properties and response characteristics of the auditory system so that when the auditory-informative stimuli are applied, such stimuli are more effective at evoking a desired auditory response, i.e., are more effective at allowing the patient to perceive sound. The information-carrying stimuli may be applied to the auditory neural system at the same time as is the non-auditory-informative stimuli, or may be applied during time slots between application of the non-auditory-informative stimuli.

16 Claims, 2 Drawing Sheets

LOW VOLTAGE STIMULATION TO ELICIT STOCHASTIC RESPONSE PATTERNS THAT ENHANCE THE EFFECTIVENESS OF A COCHLEAR IMPLANT

The present application claims the benefit of U.S. Provisional Patent Application Ser. No. 60/096,191, filed Aug. 11, 1998, which application is incorporated herein by reference.

BACKGROUND OF THE INVENTION

The present invention relates to cochlear implant systems, and more particularly to a type of stimulation applied to a patient through a cochlear implant that enhances the effectiveness of the cochlear implant.

The currently most widely used sound and speech processing strategies in cochlear implants are CIS and SPEAK. Both arc sequential pulsatile strategies, whereby each and every current pulse delivered to the auditory nerve represents a processed quantum of acoustic information that is derived from sound that has been recorded by the microphone of the cochlear implant system. Each stimulation pulse is modulated in amplitude and/or pulse width by the amount of energy and/or information that is recorded at the output of a corresponding filter and/or envelope extraction stage of the speech processor, frequently referred to as "channel". In the CIS strategy, if the output of a processing channel is zero for a given time period, the corresponding stimulation pulse will be of such amplitude as to fall below the patient's audible threshold, i.e. the pulse does not cause an auditory perception; nonetheless, it is delivered with the purpose of carrying a parcel of acoustic information (which happens to be zero at some points in time) to the auditory system.

In recent years, the modeling of acoustic nerve properties, as well as current laboratory research, indicate that better speech understanding and sound clarity for cochlear implant users may possibly be achieved by applying pulses to the auditory system at very high rates. The rationale is that very high pulse rates elicit a desirable stochastic response pattern in the auditory neural system. The purpose for generating very high stimulation rates is thus independent of the delivery of acoustic information to the auditory neural system.

Very high sequential pulse rates result in increasingly narrower pulse widths. Such increasingly narrower pulse widths make it difficult for the patient to perceive changes in loudness. This is because loudness as perceived by the patient is largely a function of charge (i.e. the combination of pulse width and pulse amplitude). In order to accomplish sufficient loudness growth with very narrow pulses, the pulse amplitude has to increase in proportion to the decrease of pulse width. Disadvantageously, very high pulse rates and ensuing narrow pulse widths are not practical for information delivery to the auditory neural system of transcutaneous cochlear implant users because of loudness growth limitations that result from limited compliance voltage. (The compliance voltage is the maximum voltage available within the cochlear implant device from which stimulation pulses may be derived.) Thus, it is seen that improvements are needed in the way high sequential pulse rates are delivered to a patient in order for such stimulation to be effective, e.g., in order to allow the patient to be able to perceive loudness.

SUMMARY OF THE INVENTION

The present invention addresses the above and other needs by providing a family of speech processing strategies for cochlear implants that includes the application of non-auditory-informative stimuli as well as auditory-informative stimuli. The non-auditory-informative stimuli is applied to the auditory neural system for the purpose of influencing the properties and response characteristics of the auditory system so that when the auditory-informative stimuli is applied, such stimuli is more effective at evoking a desired auditory response, i.e., is more effective at allowing the patient to perceive sound. The information-carrying stimuli may be applied to the auditory neural system at the same time as the non-auditory-informative stimuli, or at time slots between application of the non-auditory-informative stimuli.

In accordance with one aspect of the invention, there is provided a cochlear stimulation implant device having an electrode array attached thereto. The electrode array is adapted for insertion into the cochlea, and includes a plurality of spaced-apart electrodes formed along its length for stimulating various regions of the cochlea. The implant device includes means for sensing and generating or means for receiving auditory-informative data signals from which auditory-informative stimuli are generated and applied to selected pairs of the electrodes. The implant device also includes means for generating and applying non-auditory-informative stimuli through the electrodes. Advantageously, the non-auditory-informative stimuli elicit stochastic response patterns, or otherwise precondition and/or prepare the auditory nerve, so that application of the auditory-informative stimuli is more effective.

In accordance with another aspect of the invention, the non-auditory-informative stimuli that are used to elicit stochastic response patterns, and thereby precondition and/or prepare the auditory nerve to be more receptive to the auditory-informative stimuli, comprise low level stimuli, i.e., stimuli having an amplitude or magnitude that is essentially in the vicinity of (that is, just below or just above) the auditory threshold. As such, the preconditioning stimuli function primarily to bias the neurons of the auditory nerve so that when the auditory-informative stimuli are received, such neurons are readily triggered by the auditory-informative stimuli.

It is thus a feature of the present invention to improve the effectiveness of a cochlear implant system through application of both non-auditory-informative stimuli and auditory-informative stimuli to the auditory nerve.

It is an object of the invention to provide a cochlear stimulation device that delivers at least two types of stimuli to electrodes adapted for insertion in the cochlea: auditory-informative stimuli, and non-auditory-informative stimuli, wherein the non-auditory-informative stimuli makes application of the auditory-informative stimuli more effective.

It is a further object of the invention to provide a method of stimulating the auditory nerve that includes application of both non-auditory-informative stimuli and auditory-informative stimuli, wherein the non-auditory-informative precondition the neurons of the auditory nerve so that they are more effectively triggered by the auditory-informative stimuli when such stimuli are presented to the auditory nerve.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

In accordance with teachings of the present invention, desirable stochastic response patterns of the auditory neural system are elicited by high stimulus rates even when the stimulus amplitude is just at, or below, or slightly above, the patient's auditory threshold, and whereby the applied stimuli do not carry any acoustic information.

Figure 1:
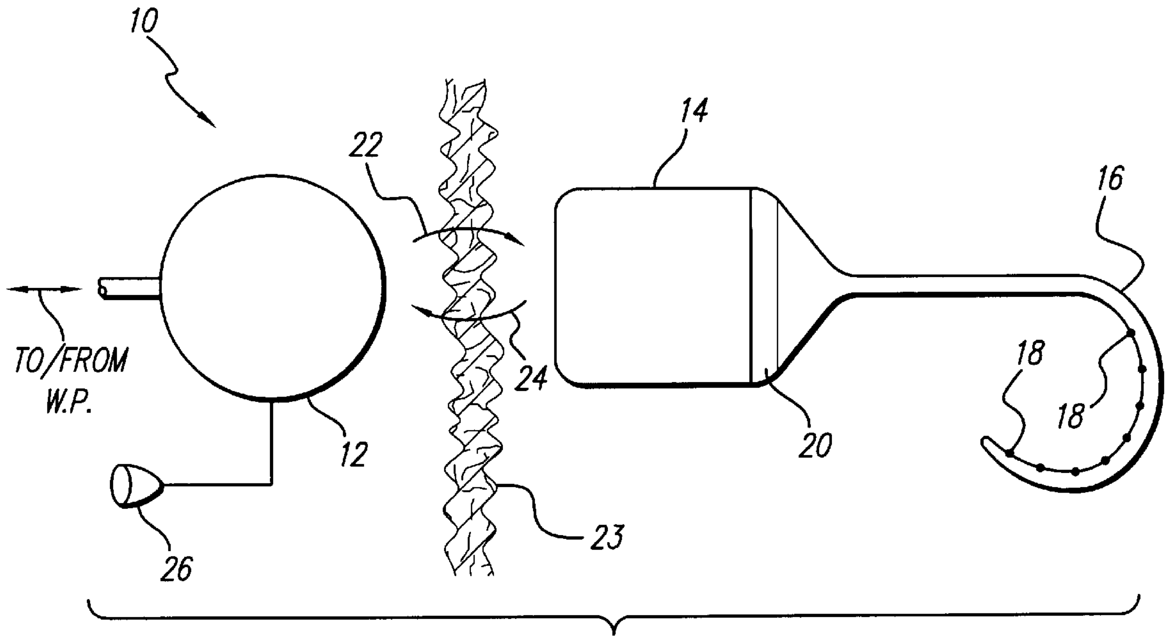
FIG. 1 shows a block diagram of a typical cochlear stimulation system.

FIG. 1 shows a block diagram of a typical cochlear stimulation system 10. The system 10 typically includes an external (non-implanted) headpiece 12 (which is usually worn behind the ear) and an implantable cochlear stimulator (ICS) 14. The ICS 14 is usually implanted under the skin 23 of the patient, in a pocket formed in the bone behind the ear. An electrode array 16, having a plurality of spaced-apart electrodes 18 thereon, is attached to the ICS 14. The electrode array 16 may be fabricated so that it naturally assumes a spiral shape, as taught in U.S. Pat. Nos. 4,686,765 and 4,819,647, incorporated herein by reference, a naturally assumes a curved shape, as taught in U.S. patent application Ser. No. 09/247,734, filed Feb. 9, 1999, assigned to the same assignee as is the present application, also incorporated herein by reference.

The electrode array 16 is adapted to be inserted into the cochlea of a patient's inner ear. A surgical tool may assist in the implantation, as taught, e.g., in U.S. Pat. No. 5,443,493, or U.S. patent application Ser. No. 09/313,901, filed May 18, 1999, assigned to the same assignee as is the present application, both of which documents are likewise incorporated herein by reference. The spiral or curved shape of the electrode array advantageously helps assure that the individual electrodes 18 are positioned adjacent or near the modiolus wall of the cochlea where they are more effective at stimulating the auditory nerve. A portion of the ICS case or housing 20 may function as a return electrode for certain stimulation modes, e.g., monopolar stimulation.

The ICS 14 is coupled to the headpiece 12 via inductive and/or rf coupling (or other suitable coupling mechanisms), allowing power and data signals 22 to be transmitted from the headpiece 12 to the ICS 14. Similarly, data signals 24 may be coupled from the ICS 14 to the headpiece 12 so that data gathered or stored within the ICS may be transmitted to an external source. The headpiece 12 typically includes, or is coupled to, a microphone 26, which microphone is used as the primary sensor for sensing acoustic pressure waves, i.e., sound.

The headpiece 12 may be coupled to a wearable processor (WP), not shown in FIG. 1. The WP, when used, includes a power source (battery) and signal processing circuitry for converting the sensed sound to suitable auditory-information signals that are transmitted to the ICS as part of the signals 22 coupled into the ICS from the headpiece, as fully described, e.g., in U.S. Pat. No. 5,603,726, incorporated herein by reference. Alternatively, for some embodiments of the invention, the signal processing circuitry of the WP, including the power source, may be included within the headpiece 12, in which case the headpiece 12 functions as a self-contained behind-the-ear (BTE) unit.

Further, in yet additional embodiments, the cochlear stimulation system may be fully implantable, as taught, e.g., in U.S. patent application Ser. No. 09/126,615, filed Jul. 31, 1998, assigned to the same assignee as is the present application, also incorporated herein by reference. In such fully implantable system, at least the ICS and speech processor (SP) are implanted, and may be housed in the same or separate housings, along with a suitable power source. In a preferred fully implantable system, the power source is rechargeable. The microphone used with the fully implantable system may or may not be implanted, but is electromagnetically coupled with the SP so that sensed audio signals can be converted to appropriate audio-informative signals by the SP in accordance with a desired speech processing strategy, and wherein such audio-informative signals may then, in turn, be converted to audio-informative stimuli by the ICS.

Figure 2:
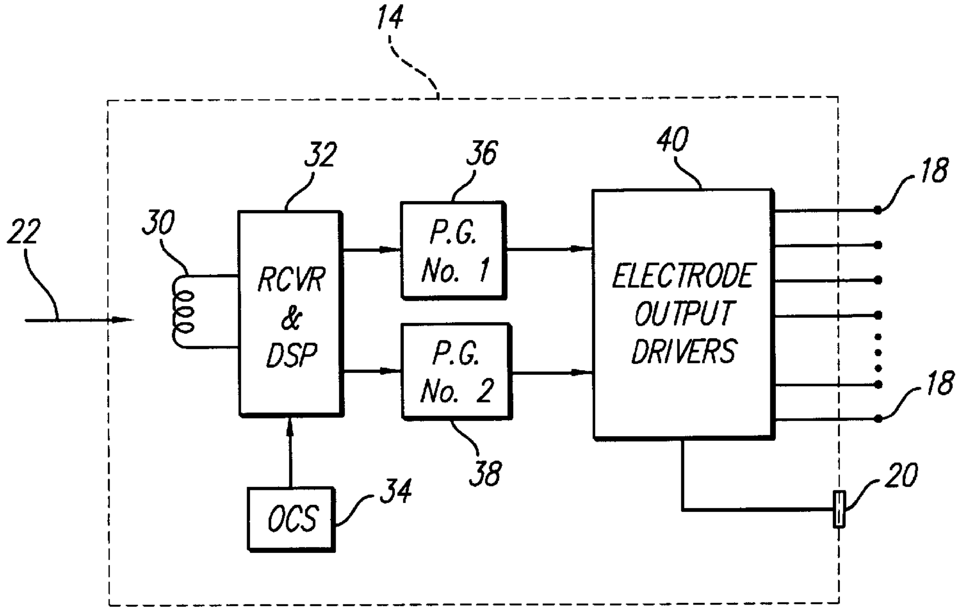
FIG. 2 is simplified functional block diagram of an implantable cochlear stimulator (ICS) made in accordance with the invention.

FIG. 2 shows a simplified functional block diagram of an implantable cochlear stimulator (ICS) 14 made in accordance with one embodiment of the invention. As seen in FIG. 2, such ICS 14 includes a coil 30 for receiving the power and data signal 22 from the external or other SP source. The signals received through the coil 30 are processed in appropriate front end receiving and digital signal processing (DSP) circuits 32. A separate oscillator circuit 34 may be employed, as required, in order to help generate high rate signals utilized by the invention for the non-auditory-informational stimuli. Alternatively, the high rate signals may be derived from the high rate carrier signal that is typically employed to transfer power into the ICS 14 from an external or other (e.g., implanted SP/power) source.

In accordance with the present invention, the DSP circuitry 32 within the ICS generates two types of stimuli for application to the electrodes 18. A first type of stimuli comprises auditory-informational stimuli, and is generated by a first pulse generator (P.G.) 36. This first type of stimuli is generated in such a way so as to convey the auditory information sensed through the microphone 26, or other sensor, to the electrodes through application of the stimuli to the electrodes in accordance with a selected speech processing strategy. A second type of stimuli comprises high-rate non-auditory information stimuli, and is generated by a second pulse generator 38. The second type of stimuli preferably has a magnitude that is close to the auditory threshold, i.e., in the vicinity of the auditory threshold (just below or just above the threshold), and is therefore not perceived by the user. Advantageously, the second type of stimuli preconditions or biases the neurons of the auditory nerve so that the first type of stimuli is more effective at triggering such neurons with the auditory information when the first type of stimuli is presented to the auditory nerve. In order to accomplish this goal—of preconditioning the auditory neurons so that they are more receptive to being triggered by the auditory-informative first type of stimuli—the second type of stimuli must be applied to the neurons either before, or at least concurrent with, the application of the first type of stimuli, as taught more fully below in FIG. 3.

Both the first type of stimuli, i.e., the auditory-informational stimuli, and the second type of stimuli, i.e., the non-auditory-information stimuli, are applied to selected pairs of electrodes through electrode output driver circuitry 40. Representative electrode output circuitry is depicted in U.S. Pat. No. 5,603,726, or alternatively in U.S. patent application Ser. No. 09/338,700, filed Jun. 23, 1999, entitled "Programmable Current output Stimulus Stage for Implantable Device", assigned to the same assignee as is the present application, which application is incorporated herein by reference.

It is thus seen that the present invention is directed, in a broad sense, to a new type of speech processing strategy wherein the auditory information-bearing content of a stimulation signal is combined with non-auditory stimulation information. Advantageously, the non-auditory stimulation information preconditions or otherwise prepares the tissue being stimulated with the auditory information-bearing stimuli so that it is more receptive to such auditory information-bearing stimuli.

By way of example, the non-auditory-information stimuli is configured (i.e., its pulse width, amplitude, and repetition frequency is selected) to elicit stochastic response patterns from the auditory nerves that enhance the effectiveness of application of the auditory-information content stimuli. Such goal is best achieved in accordance with the present invention when the non-auditory-information stimuli is selected to have narrow pulse widths, low amplitudes, and high repetition rates as compared to the auditory-information stimuli. The repetition rate of the non-auditory-information stimuli is typically at least 5 kHz and may be greater. The pulse width of the non-auditory-information stimuli is generally selected to be less than 100 microseconds, and may be as narrow as 5–10 microseconds. The amplitude of the non-auditory-information stimuli is selected to be near, and preferably just less than, the auditory perception threshold of the patient. For example, if the auditory perception threshold at the selected frequency and pulse width is determined to be 200 millivolts, then the amplitude of the non-auditory-information signal should be selected to be within about 10% of such threshold, e.g., between 180 and 220 millivolts.

While FIG. 2 suggests that the two types of stimuli are generated using circuitry housed within the ICS for delivery to electrodes attached to the ICS, it is to be understood that at least one or both of the two types of stimuli (or at least control signals that define such two types of stimuli) may also be generated in circuitry external to the ICS. That is, signals defining one or both types of stimuli, i.e., non-auditory-informative stimuli, as well as auditory-informative stimuli, may be generated in a behind-the-ear speech processor, or within an external wearable processor, or within a separate implantable unit coupled to the ICS. In such instances, the circuitry within the ICS merely receives the stimulus-defining control signals, and then applies stimuli to the electrodes in accordance with such received stimulus-defining control signals. In other words, the speech processing strategy defined by the present invention may be generated and applied either in the implant device(s), or in the external device(s), or in combinations of the implant and external devices.

Figure 3:
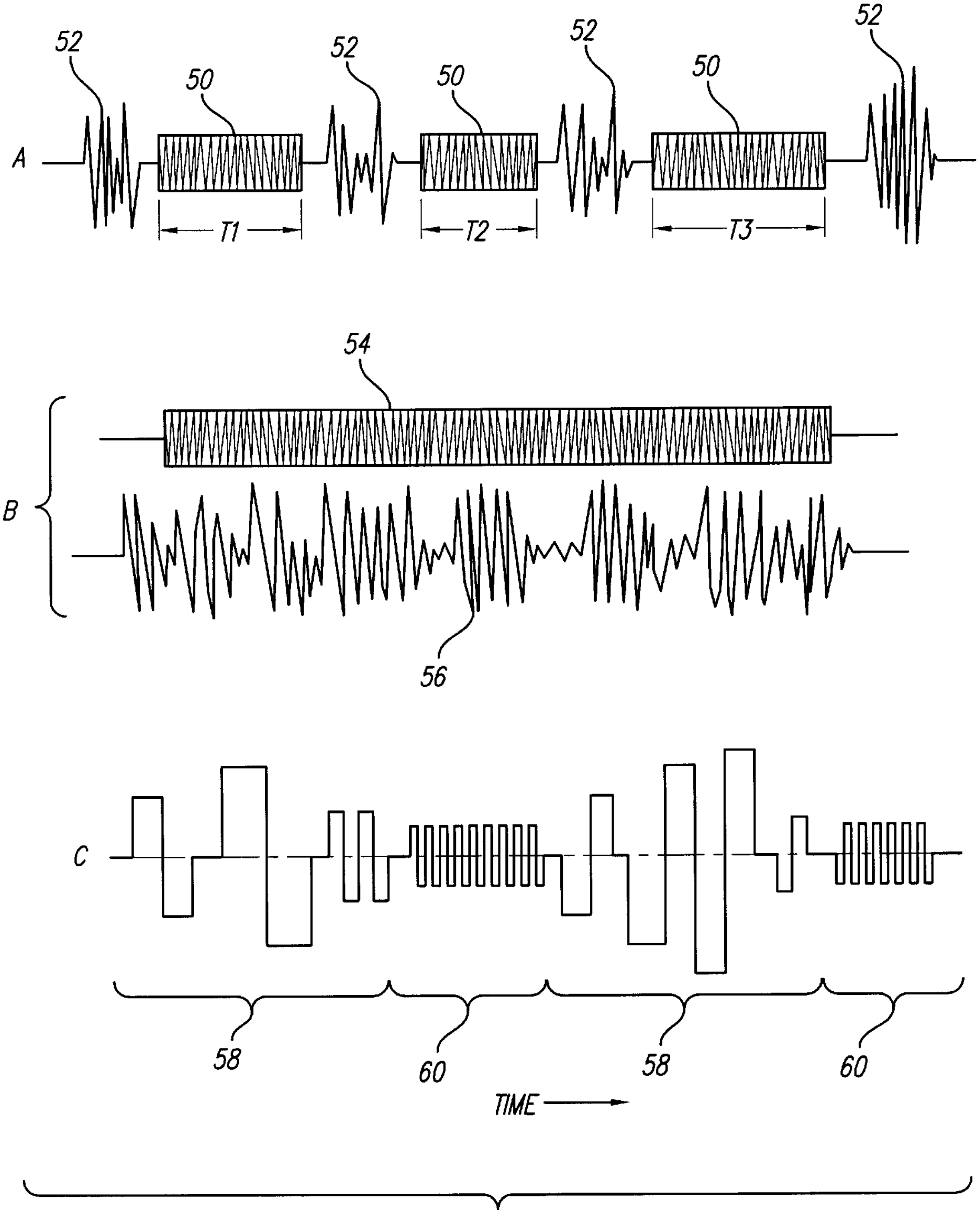
FIG. 3 is a timing diagram that conceptually illustrates different ways in which the auditory-informative and non-auditory-informative stimuli may be applied to the electrodes of the ICS in accordance with the invention.

FIG. 3 shows some non-limiting examples of ways in which the auditory-informative and non-auditory-informative stimuli may be applied to the electrodes of the ICS in accordance with the invention. As indicated previously, the invention contemplates that narrow stimuli (stimulus pulses having a narrow pulse width) with limited amplitude so as to result in very low loudness perception or no auditory perception at all, be interspersed with regular, auditory-information-delivering stimuli that have more charge carrying capability (such as biphasic pulses with greater pulse widths) and are thus suitable to amplitude modulation so as to result in loud, audible perception. Hence, as shown in the top line of the timing diagram of FIG. 3, designated "A", the narrow low-charge non-informative stimuli 50 may be interspersed sequentially, i.e. occur between information carrying stimuli 52. That is, the non-informative stimuli 50 are delivered to the appropriate electrodes so as to occur during time windows or time periods T1, T2, or T3 during which the informative stimuli 52 do not appear. In one embodiment, the time windows T1, T2 and/or T3 (during which non-informative stimuli are applied to the electrodes) occur at those points in time within the stream of normal informative stimuli 52 when the sound or speech information content of the stimuli 52 is at a minimum, i.e., at those "lull" or "pause" points during most speech/sound signals when little information is conveyed.

In another embodiment, shown, e.g., in line "C" of FIG. 3, the time windows 60 during which the non-informative stimuli are applied are themselves very short, so as not to cause any significant perceptible disruption to the informative stimuli 58 which are applied to the electrodes. Thus, it is seen that line "C" of FIG. 3 illustrates a variation of the sequential interspersed approach shown in line "A" wherein a few pulses of information carrying stimuli 58, which are generally wider biphasic pulses, are interspersed with many cycles of narrow, non-informational pulses 60.

Alternatively, non-informative stimuli 54 may occur on one or more passive channels at the same time that an information carrying stimuli 56 are delivered to another channel, as shown in line "B" of FIG. 3. This type of stimuli application requires the implant system have multiple current sources and simultaneous stimulation capability of multiple electrodes.

Those of skill in the art, given the teachings presented herein, may readily fashion other types of speech processing strategies, each employing non-auditory-informational pulses having sub-threshold, near- or at-threshold magnitude, as well as auditory informational pulses. That which is shown in FIG. 3 is intended to be exemplary, not limiting.

While the invention herein disclosed has been described by means of specific embodiments and applications thereof, numerous modifications and variations could be made thereto by those skilled in the art without departing from the scope of the invention set forth in the claims.

What is claimed is:

1. A cochlear stimulation implant device comprising:

an electrode array adapted for insertion into the cochlea;

a plurality of spaced-apart electrodes on the electrode array;

first means for generating auditory-informative stimuli and applying such stimuli to selected pairs of the electrodes;

second means for generating non-auditory-informative stimuli and applying the non-auditory-informative stimuli to selected pairs of the electrodes;

wherein the non-auditory-informative stimuli have a magnitude that is substantially no greater than an auditory perception threshold level, and further wherein the non-auditory-informative stimuli bias or precondition auditory neurons so that application of the auditory-informative stimuli to the auditory neurons is more effective.

2. The cochlear stimulation implant device of claim 1 wherein the non-auditory-informative stimuli and the auditory-informative stimuli are interspersed in a single stimulation channel.

3. The cochlear stimulation implant device of claim 1 wherein the non-auditory-informative stimuli and the auditory-informative stimuli are applied simultaneously to parallel stimulation channels.

4. The cochlear stimulation implant device of claim 1 wherein the non-auditory-informative stimuli comprise fast sequential stimuli that enhance stochastic response patterns and thereby enhance the effectiveness of the auditory-informative stimuli.

5. The cochlear stimulation implant device of claim 4 wherein the fast sequential stimuli used as the non-auditory-informative stimuli have a frequency above 5 kHz.

6. The cochlear stimulation implant device of claim 4 wherein the fast sequential stimuli used as the non-auditory-informative stimuli have a pulse width less than 100 microseconds.

7. A cochlear stimulation system comprising:

a plurality of spaced apart electrodes configured for insertion into the cochlea;

a stimulus pulse generator connected to the electrodes that generates auditory-informative stimuli and non-auditory-informative stimuli responsive to control signals;

a control circuit coupled to the stimulus pulse generator that generates the control signals which cause the stimulus pulse generator to apply both the auditory-informative stimuli and the non-auditory-informative stimuli to selected electrodes of the plurality of spaced-apart electrodes, and wherein the non-auditory-informative stimuli have a pulse width, pulse amplitude and repetition rate selected to condition tissue and nerves receiving such non-auditory-informative stimuli so that application of the auditory-informative stimuli to the same or adjacent tissue is more effective.

8. The cochlear stimulation system of claim 7 wherein the pulse width, pulse amplitude and repetition rate of the non-auditory-informative stimuli are selected, as a combination, to provide stimuli to a user of the cochlear stimulation system that is not noticeably perceptible.

9. The cochlear stimulation system of claim 8 wherein the pulse width of the non-auditory-informative stimuli is no greater than 100 microseconds and the repetition rate is at least 5 KHz.

10. The cochlear stimulation system of claim 7 wherein the stimulus pulse generator and control circuit are housed within hermetically sealed housings which are implantable.

11. A method of stimulating the auditory nerve from inside the cochlea, the auditory nerve having an auditory perception threshold, the method comprising:

(a) implanting a cochlear electrode array inside of the cochlea, the electrode array having a plurality of spaced-apart electrodes thereon;

(b) applying non-auditory-informative stimuli having pulse width, pulse amplitude and repetition rate characteristics having a magnitude that is substantially greater than the auditory perception threshold to selected electrodes of the electrode array; and (c) applying auditory-informative stimuli to selected electrodes of the electrode array.

12. The method of claim 11 wherein steps (b) and (c) comprise applying the non-auditory-informative stimuli and the auditory-informative stimuli to the same electrodes by interspersing the non-auditory-informative stimuli with the auditory-informative stimuli.

13. The method of claim 11 wherein steps (b) and (c) comprise applying the non-auditory-informative stimuli to one set of electrodes within the electrode array simultaneously with applying the auditory-informative stimuli to another set of electrodes within the electrode array.

14. The method of claim 11 wherein the repetition rate, pulse width, and pulse amplitude of the non-auditory-informative stimuli are selected to enhance stochastic response patterns of auditory neurons for the purpose of enhancing the effectiveness of the auditory-informative stimuli applied in step (c).

15. The method of claim 14 wherein step (b) comprises applying non-auditory-informative stimuli having a frequency of at least 5 KHz.

16. The method of claim 14 wherein step (b) comprises applying non-auditory-informative stimuli having a pulse width of no more than 100 microseconds.

* * * * *